United States Patent
Pan et al.

(10) Patent No.: US 6,504,894 B2
(45) Date of Patent: Jan. 7, 2003

(54) PHASE-DRIVEN MULTISECTOR RECONSTRUCTION FOR MULTISLICE HELICAL CT IMAGING

(75) Inventors: Tin-Su Pan, Brookfield, WI (US); Yun Shen, Tokyo (JP)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/966,306

(22) Filed: Sep. 28, 2001

(65) Prior Publication Data

US 2002/0136350 A1 Sep. 26, 2002

Related U.S. Application Data

(60) Provisional application No. 60/237,097, filed on Sep. 29, 2000.

(51) Int. Cl.[7] .................................................. A61B 6/03
(52) U.S. Cl. ............................... 378/8; 378/15; 378/901
(58) Field of Search ........................... 378/4, 8, 15, 95, 378/901

(56) References Cited

U.S. PATENT DOCUMENTS

| | | |
|---|---|---|
| 3,954,098 A | 5/1976 | Dick et al. |
| 4,547,892 A | 10/1985 | Richey et al. |
| 4,630,202 A | 12/1986 | Mori |
| 4,994,965 A | 2/1991 | Crawford et al. |
| 5,262,946 A | 11/1993 | Heuscher |
| 5,287,276 A | 2/1994 | Crawford et al. |
| 5,383,231 A | 1/1995 | Yamagishi |
| 6,243,437 B1 * | 6/2001 | Hu et al. ...................... 378/8 |
| 6,353,653 B1 * | 3/2002 | Edic ............................. 378/4 |

FOREIGN PATENT DOCUMENTS

EP    0 983 747 A1    3/2000

OTHER PUBLICATIONS

International Search Report, dated May 3, 2002, Application No. PCT/US 01/30583, 3 pages.

* cited by examiner

Primary Examiner—David V. Bruce
(74) Attorney, Agent, or Firm—Carl B. Horton, Esq.; Armstrong Teasdale LLP (57) ABSTRACT

One aspect of the present invention is a method for multisector computed tomographic (CT) imaging of a cyclically moving object, including steps of: helically scanning a cyclically moving object with a CT imaging system having multiple detector rows and a rotating gantry, at a gantry rotation speed selected either to lead or to lag a cycle of the cyclically moving object; retrospectively gating the projection data of the object with a gating signal related to the motion of the cyclically moving object so that a geometric phase difference is created between a cycle of the rotating gantry and the motion of the cyclically moving object; and reconstructing an image of the cyclically moving object using gated sector data from image data representing a plurality of consecutive cycles of the cyclically moving object.

20 Claims, 11 Drawing Sheets

3.6 sectors for 63.2 bpm and 0.8 sec rotation

PHASE-DRIVEN MULTISECTOR RECONSTRUCTION FOR MULTISLICE HELICAL CT IMAGING

CROSS REFERENCE TO RELATED APPLICATION

This application claims the benefit of U.S. Provisional Application No. 60/237,097, filed Sep. 29, 2000.

BACKGROUND OF THE INVENTION

This invention relates generally to methods and apparatus for processing computed tomographic (CT) images, and more particularly to methods and apparatus for improving temporal resolution of CT images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Some applications of CT imaging use gated CT data. For example, in some cardiac imaging applications, projection data is retrospectively gated by a patient EKG signal. With retrospective gating, projection data of each cardiac cycle is divided into multiple bins, each of which covers a small portion of the cardiac cycle. In known gated CT applications, temporal resolution and signal to noise ratio are limited.

For example, a multi-detector row CT (MDCT) imaging system is used with a fast scan pitch of 3:1 to 6:1 and with a high gantry rotation speed $G_s$ in the sub-second range. Exemplary rotation rates of known CT imaging systems include rotation rates of 0.5 and 0.8 sec per rotation. When a half scan reconstruction (HSR) is used for improving temporal resolution of the reconstructed image, the temporal resolution $T_r$ is:

$$\frac{1}{2} = \frac{\pi + \gamma}{2\pi} G_s, \quad [1]$$

where the fan angle of detector arc is $\gamma$, and the half scan reconstruction uses only data of $\pi+\gamma$ view coverage or gantry rotation to reconstruct an image. The temporal resolution is a function of both fan angle $\gamma$ and $G_s$. For example, with $G_s$=0.5 sec and $\gamma$=60°, $T_{1/2}$=330 msec, which may not be sufficient to image the heart at its diastole phase. It would therefore be desirable to collect data from multiple cardiac cycles to improve the temporal resolution and/or signal to noise ratio of the reconstructed image.

BRIEF SUMMARY OF THE INVENTION

There is therefore provided, in one aspect of the present invention, a method for multisector computed tomographic (CT) imaging of a cyclically moving object, including steps of: helically scanning a cyclically moving object with a CT imaging system having multiple detector rows and a rotating gantry, at a gantry rotation speed selected either to lead or to lag a cycle of the cyclically moving object; retrospectively gating the projection data of the object with a gating signal related to the motion of the cyclically moving object so that a geometric phase difference is created between a cycle of the rotating gantry and the motion of the cyclically moving object; and reconstructing an image of the cyclically moving object using gated sector data from image data representing a plurality of consecutive cycles of the cyclically moving object.

Where the cyclically moving object is a patent's heart, this embodiment allows a non-invasive cardiac CT examination to be achieved in a single breath-hold with either a non-contrast enhanced scan to demonstrate the calcification deposit at various coronary arteries, or a contrast enhanced scan to depict the anatomical structure of the coronary artery and to assess dynamic functions of the heart such as ejection fraction, wall motion and valvular function.

The above-described embodiment of the present invention also provides substantial improvement in resolution because the phase difference or temporal resolution can be made as short as 100 msec to freeze the cardiac motion in diastole. Embodiments of the present invention are particularly useful in patients without arrhythmia.

DETAILED DESCRIPTION OF THE INVENTION

Figure 1:
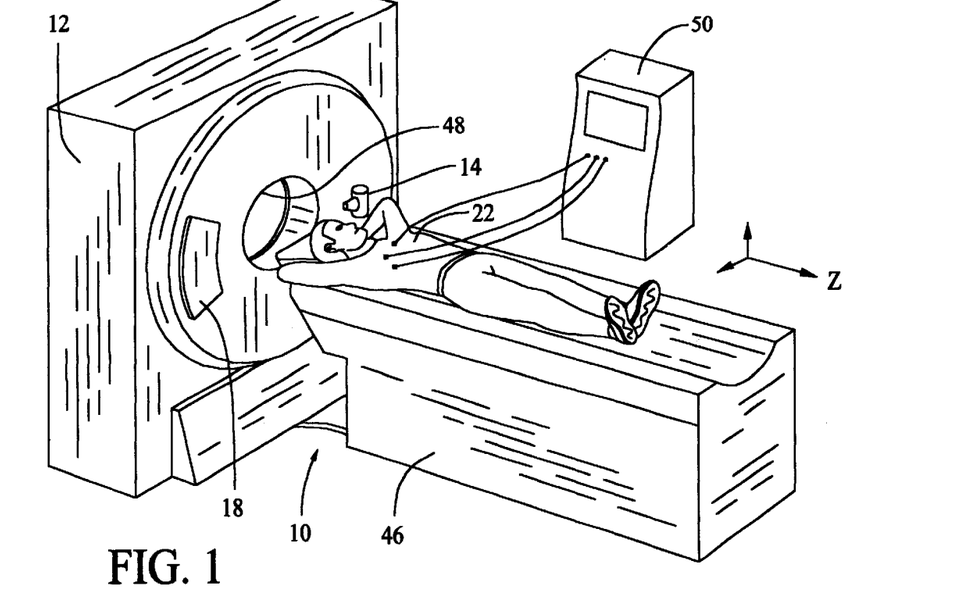
FIG. 1 is a pictorial view of a CT imaging system.
Figure 2:
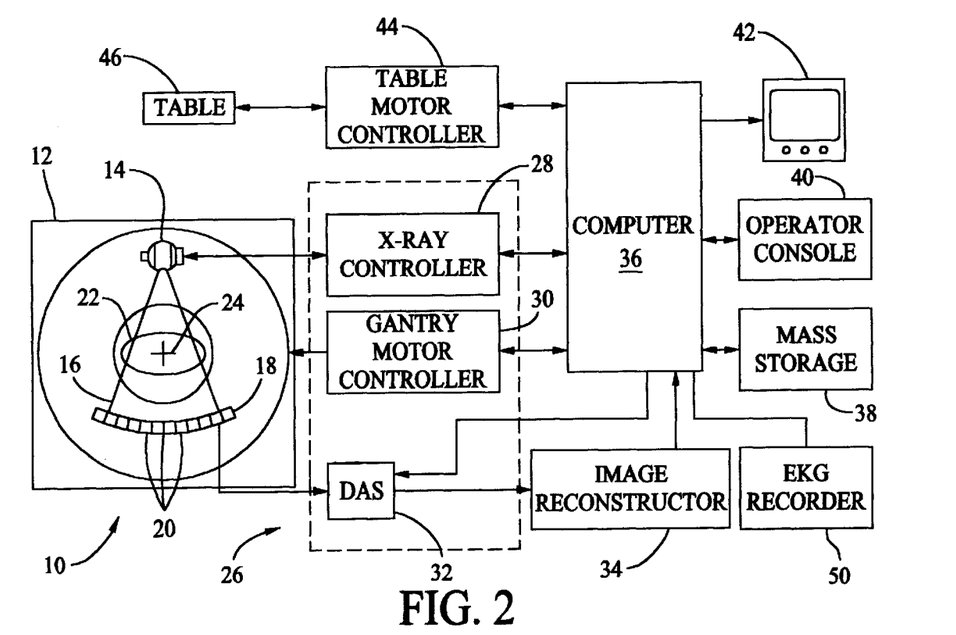
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2. One or more additional rows of detector elements 20 in such configurations are arranged parallel to the illustrated row, and each row is transverse to the translation direction of patient 22 (i.e., the z-axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan, table 46 moves while projection data is being collected and gantry 12 is rotating.

One embodiment of the present invention is a multi-sector reconstruction (MSR) technique utilizing both the fast scan speed and large z-coverage of multiple detector-row CT (MDCT) is used to image the heart at a temporal resolution close to 100 msec. Retrospective EKG gating is used to improve temporal resolution of the reconstructed image.

Figure 3:
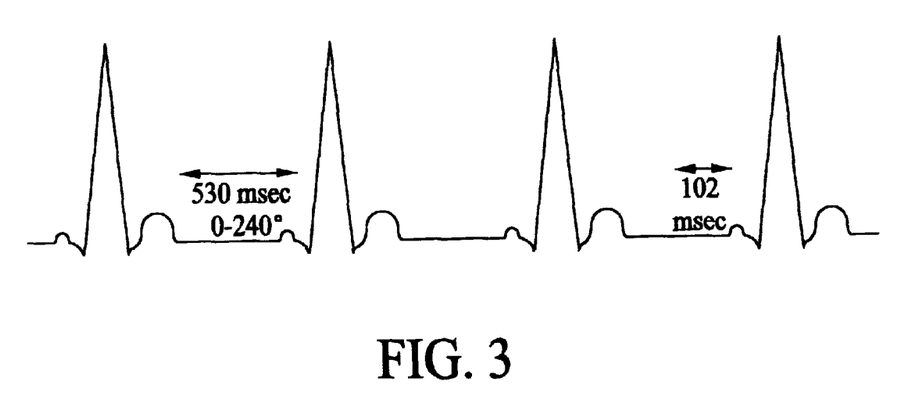
FIG. 3 is a representation of an EKG signal with gating, showing the improvement possible in CT imaging when reconstructing an image of 530 msec resolution vs. reconstructing using gating of the same phase from four cardiac cycles.

In one embodiment of the present invention, cardiac imaging is accomplished by retrospectively gating helically-scanned CT imaging data using a signal recorded from an EKG machine 50 monitoring the cardiac cycles of patient 22. Patient 22 holds his breath while a helical CT imaging scan is performed. Multiple detector rows of array 18 are used in imaging system 10 along with sub-second gantry 12 rotation rates, resulting in gantry 12 rotation that is out of phase with cardiac motion. This out-of-phase rotation generates a geometric phase difference between the gantry rotation and the heart motion of patient 12. A temporal window is defined by an amount of time needed for gantry 12 rotation to cover this phase difference. Different geometric phases from multiple cardiac cycles are then combined to process data for image reconstruction. The improvement can be quite dramatic because phase differences or temporal resolution can be as short as 100 msec in some embodiments, to freeze cardiac motion in diastole. The cardiac cycles in FIG. 3 illustrate how an improvement in temporal resolution can be obtained by reducing the temporal window from 530 msec to 132 msec. In the latter case, gated data from four cardiac cycles is used. (These additional cardiac cycles are not shown in FIG. 3.)

For example, a multi-detector row CT (MDCT) imaging system 10 is used with a fast scan pitch of 3:1 to 6:1 and with a high gantry 12 rotation speed in the sub-second range. Exemplary rotation rates include rotation rates of 0.5 and 0.8 sec per rotation, as well as other rotation rates ranging from 0.5 sec per rotation to 1.0 sec per rotation. As described above, if a half scan reconstruction (HSR) were used for improving temporal resolution of the reconstructed image, the temporal resolution $T_r$ would be $T_{1/2}$ as given in Eq. 1, where the fan angle of detector arc is γ, and the half scan reconstruction uses only data of π+γ view coverage or gantry 12 rotation to reconstruct an image. The temporal resolution is a function of both fan angle γ and gantry rotation speed $G_s$. (By convention, gantry rotation speed $G_s$ as used herein always refers to the number of seconds required per revolution of gantry 12. Thus, 0.8 sec refers to a speed of 0.8 seconds per revolution.) In the example discussed above, $T_{1/2}$=330 msec, which may not be sufficient to image the heart at its diastole phase. By contrast, multi-sector reconstruction of one embodiment of the present invention uses the periodicity of heart motion and EKG gating to improve $T_r$ to as fast as 100 msec.

When gantry rotation cycle is not in phase with the cardiac motion cycle, a geometric phase difference is created between the gantry rotation cycle and the heart motion cycle.

Thus, one embodiment of the present invention combines different geometric phases from multiple cardiac cycles to make up data of $\pi+\gamma$ for image reconstruction. Temporal resolution $T_r$ in this embodiment is thus the time needed for the gantry rotation to cover this phase difference.

The improvement in $T_r$ over $T_{1/2}$ is substantial. The value of $T_m$ for the multi-sector reconstruction is be in the neighborhood of 100 msec or less in one embodiment of the present invention:

$$T_m = \left| G_s - \frac{60}{B} \right|, \quad [2]$$

where B is heart rate in beats per minute (bpm), and $G_s$ is the gantry 12 rotation speed in seconds per revolution.

When an ideal gantry speed is selected, an improvement of a factor of 4 is achieved for $T_r$ such that $$T_m = \frac{1}{4} T_{\frac{1}{2}}. \quad [3]$$

From Eq. 1, with $\gamma=60°$, $$T_{\frac{1}{2}} = \frac{2}{3} G_s, \quad [4]$$

and $$T_m = \frac{1}{6} G_s. \quad [5]$$

Therefore, two ideal gantry speeds derived from Eqs. 2 and 5 and used in some embodiments of the present invention are:

$$G'_s = \frac{360}{7B}, \text{ and } G_s^\dagger = \frac{360}{5B}. \quad [6]$$

Figure 4:
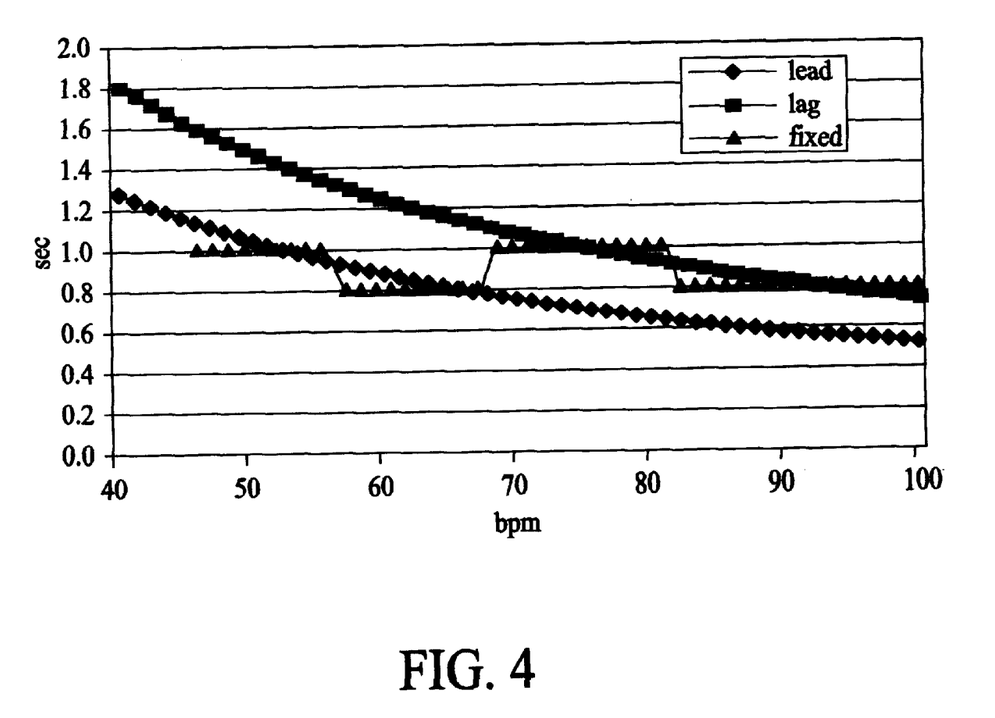
FIG. 4 is a representation of two ideal gantry speeds with respect to different heart rates, as well as a gantry speed selection for an imaging system having only two gantry speeds of 0.8 and 1.0 sec.

Representations of these two gantry speeds are shown in the graph of FIG. 4 with respect to various heart rates. The $G'_s$ graph is always leading the cardiac cycle, and is shown as such, whereas $G_s^\dagger$ is lagging the cardiac cycle, and is shown as such. (The "fixed" trace in FIG. 4 corresponds to a closest approximation to an ideal speeds obtained by an imaging system 10 having only two gantry 12 rates, 0.8 seconds per rotation and 1.0 seconds per rotation.)

The number of cardiac cycles ($n_s$) needed to provide data for an image reconstruction of temporal resolution $T_m$ is $$n_s = \frac{T_{\frac{1}{2}}}{T_m}, \quad [7]$$

$$= \frac{(\gamma + \pi)}{2\pi} \frac{G_s}{T_m}. \quad [8]$$

The $n_s$ is inversely proportional to the temporal resolution $T_m$, and $T_m$ is a function of both B and $G_s$ and $G_s$ in Eq. 2. For ideal gantry speeds of $G'_s$ and $G_s^{554}$, $n_s$=4. Thus, in one embodiment, the gantry 12 rotation speed tracks the heart rate thereby maintaining the same number of sectors for reconstruction, and obtaining the temporal resolution of Eq. 3.

Figure 5:
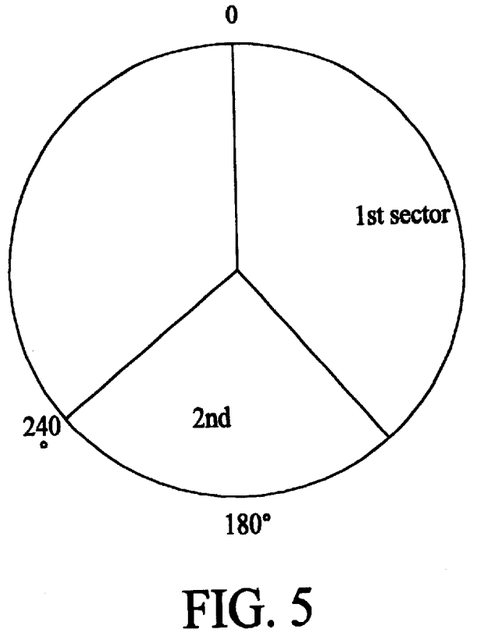
FIG. 5 is a representation of a sector size selection for a temporal resolution $T_m$ of 290 msec, a number of cardiac cycles $n_s$ of 1.8 when the gantry rotation speed $G_s$ is 0.8 sec per revolution and the heart rate B is 55 bpm.

In another embodiment, imaging system 10 provides a limited number of gantry speed selections. Thus, $n_s$ can vary significantly with respect to B. For one such imaging system 10, $G_s$=0.8 or 1.0 sec. From Eqs. 2 and 8 with the two gantry speeds, there are several possibilities for any given B and a chosen $G_s$:

When $T_m$ is large, $n_s$ may be as small as 1 to 2. In this case, image reconstruction depends on the data from only 1 to 2 consecutive cardiac cycles, and is less sensitive to the variation of the periodicity of heart motion in these 1 to 2 cardiac cycles. Another example is $n_s$=1.8 with $T_m$=290 msec, when B=55 bpm and $G_s$=0.8 sec, as represented in FIG. 5. (Each sector represents projection data acquired during rotation of gantry 12 through a specified portion of a revolution relative to a reference position.)

Figure 6:
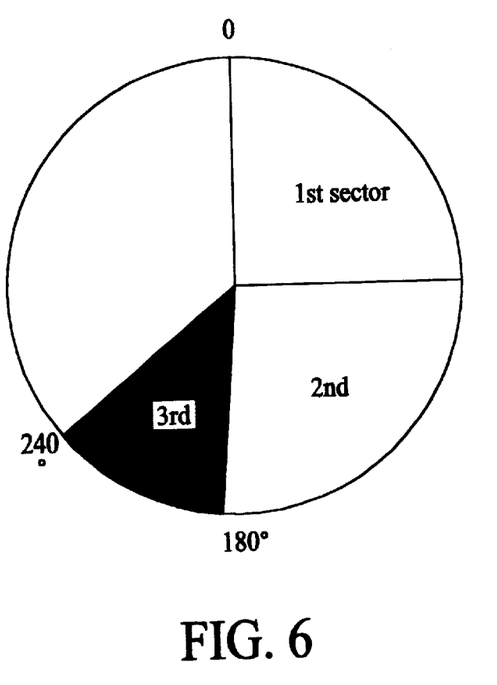
FIG. 6 is a representation of a sector size selection for $T_m$=200 msec, $n_s$=2.6 when $G_s$=0.8 sec and B=60 bpm.
Figure 7:
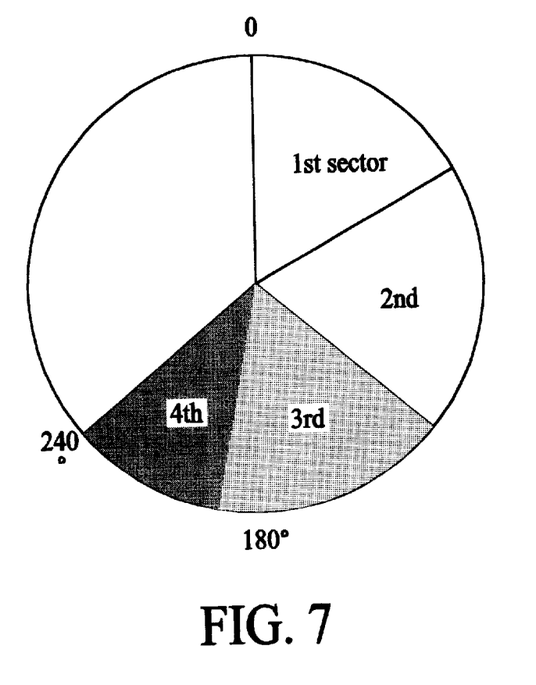
FIG. 7 is a representation of a sector size selection for $T_m$=140 msec, $n_s$=3.8 when $G_s$=0.8 sec and B=64 bpm.

When $T_m$ is small and $n_s$ is in the range of 2 to 4, there is a significant improvement of $T_m$ over $T_m$ of 2 to 4 times. An image reconstruction is dependent on the consecutive 2 to 4 cardiac cycles, and the irregularity of cardiac motion in the consecutive 2 to 4 cardiac cycles may introduce artifacts in the image from inconsistency of the cardiac motion. However, some stability of heart rate in 2 to 4 cardiac cycles is shown in patient data. Examples are $n_s$=2.6 with $T_m$=200 msec, when B=60 bpm and $G_s$=0.8 sec, as represented in FIG. 6; and $n_s$=3.8 with $T_m$=140 msec, when B=64 bpm and $G_s$=0.8 sec, as in FIG. 7.

When $T_m$ is very small and $n_s$ is greater than 4, multi-sector reconstruction may be less effective when stability of cardiac cycles is at issue and when the spread of data in the patient table direction is too broad. In such cases, data inconsistency in the table direction of helical data may result. Therefore, in one embodiment of the present invention, a hard limit of 4 is set on $n_s$ to improve stability of reconstruction with faster coverage in helical mode and less improvement on $T_m$. To restrict $n_s \leq 4$ in this embodiment, an equal expansion of the first and last sectors of the 4 sectors is allowed, so that a necessary data range for an image reconstruction is covered. In this embodiment, the first and last sectors have a temporal window of $$T_m = 0.5 \times T_{1/2} - T_m. \quad [9]$$

Since these four sectors only overlap in phase of $T_m$, the overall $T_r$ is given by:

$$T = T_{1/2} - T_m. \quad [10]$$

Figure 8:
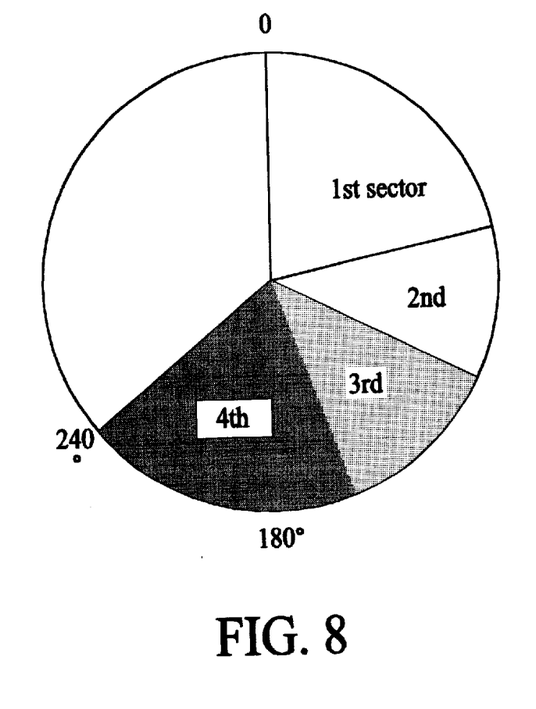
FIG. 8 is a representation of a sector size selection for $T_m$=280 msec, $n_s$=4 when $G_s$=0.8 sec and B=68 bpm.
Figure 9:
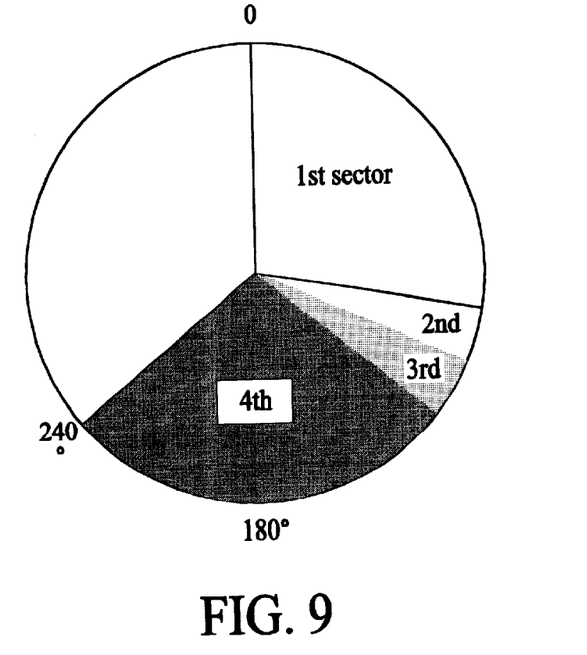
FIG. 9 is a representation of a sector size selection for $T_m$=420 msec, $n_s$=4 when $G_s$=0.8 sec and B=72 bpm.
Figure 10:
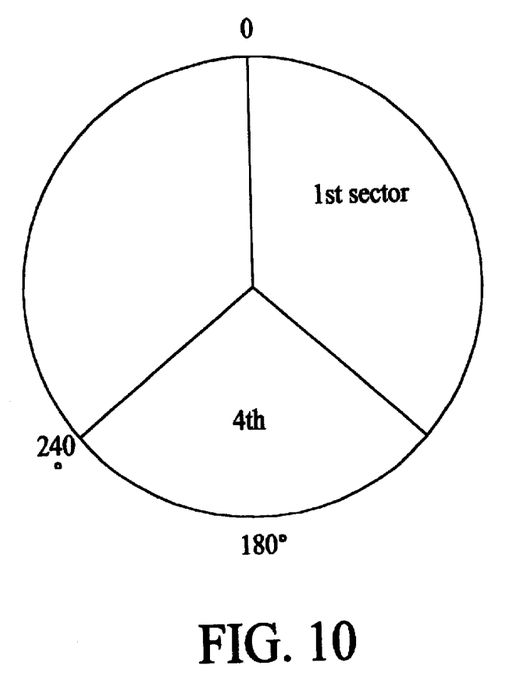
FIG. 10 is a representation of a sector size selection for $G_s$=1 sec and B=60 bpm or $G_s$=0.8 sec and B=75 bpm.

One example is $n_s \leq 4$ with $T_m$=280 msec, as represented in FIG. 8, to replace the more stringent requirement of $n_s$=6.3 with $T_m$=82 msec, when B=68 bpm and $G_s$=0.8 sec. Another example is $n_s \leq 4$ with $T_m$=420 msec, as represented in FIG. 9, to replace the requirement for $n_s$=15.7 with $T_m$=34 msec when B=72 bpm and $G_s$=0.8 sec. When gantry speed synchronizes with heart cycle such as B=60 bpm and $G_s$=1, or when B=75 bpm and $G_s$=0.8 sec, then $n_s$=2 and reconstruction becomes very similar to half scan reconstruction with $T_m$=$T_{1/2}$, as represented in FIG. 10.

Figure 11:
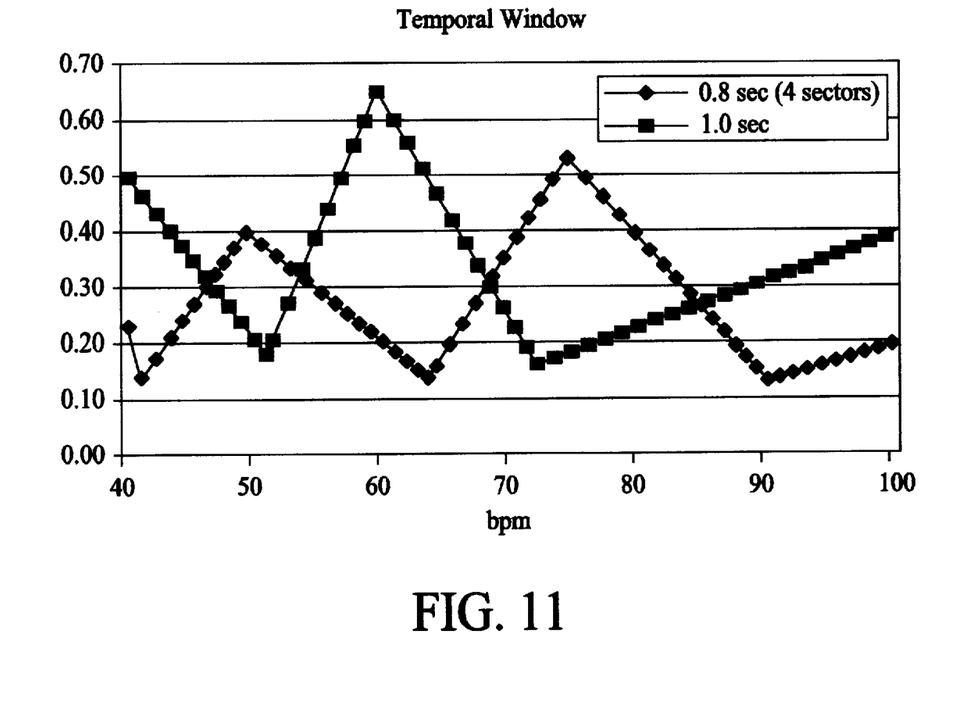
FIG. 11 is a graph showing the relation between temporal resolution $T_r$ and heart rate B with respect to two gantry rotation rates between 0.8 seconds per revolution and 1.0 second per revolution, the illustration showing that the 1.0 second per revolution speed is preferable for heart rates between 46 to 54 bpm and between 68 to 83 bpm, whereas at other rates, 0.8 seconds per revolution is preferable.

FIG. 11 shows the temporal resolution of $T_m$ with respect to gantry speeds of 0.8 and 1.0 secs. Selection of $G_s$ is important for MSR because a good selection of $G_s$ and B provides a sufficient improvement of $T_m$ to freeze cardiac motion at diastole. The $T_m$ is a function of both the $G_s$ and B and is bounded by the $T_{1/2}$ which is a function of $G_s$ in Eq. 1. One embodiment of the present invention uses a moving average of 4 consecutive heart rates to determine the $n_s$ for sector selection.

Figure 12:
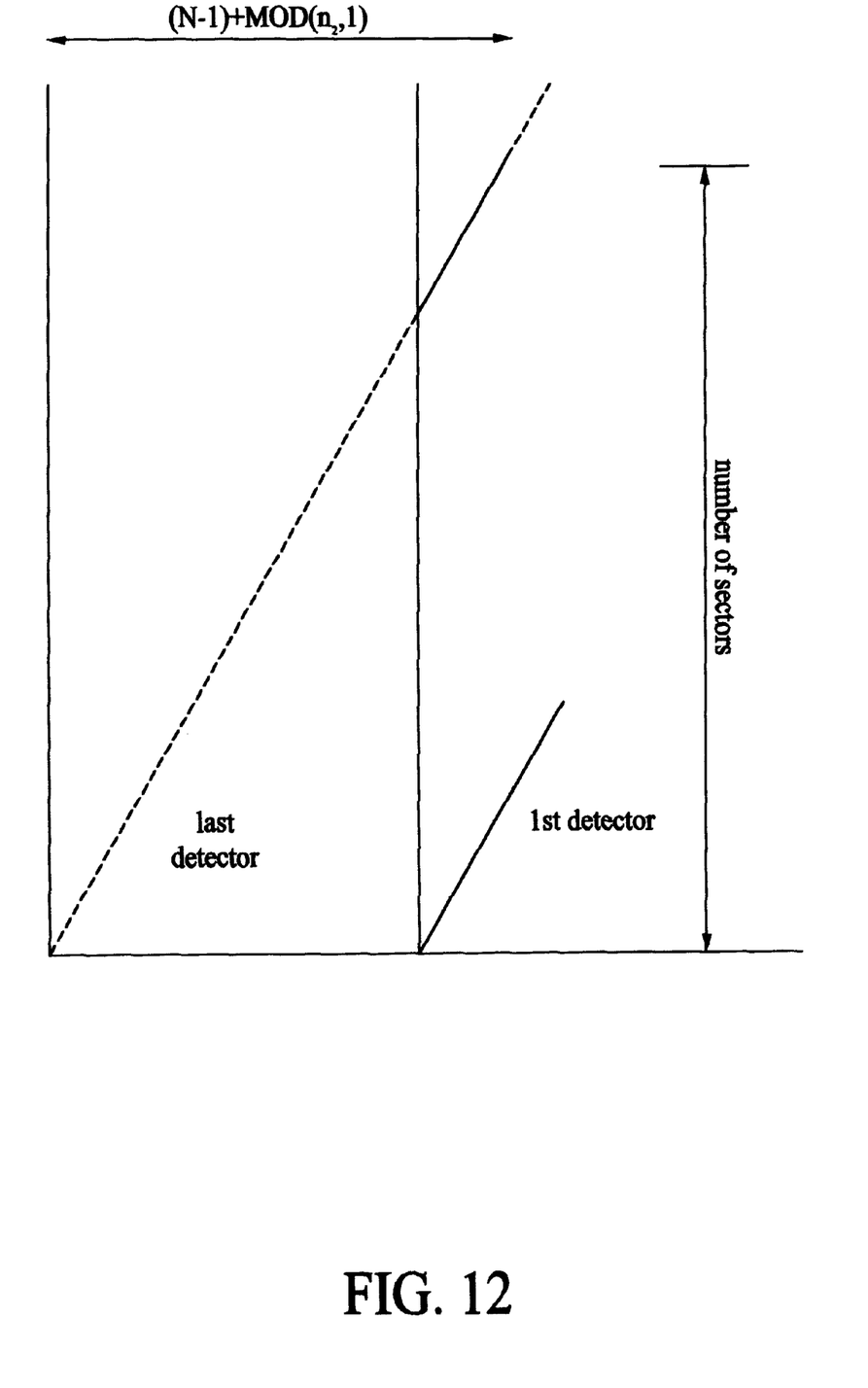
FIG. 12 is a diagram showing a pitch calculation.
Figure 13:
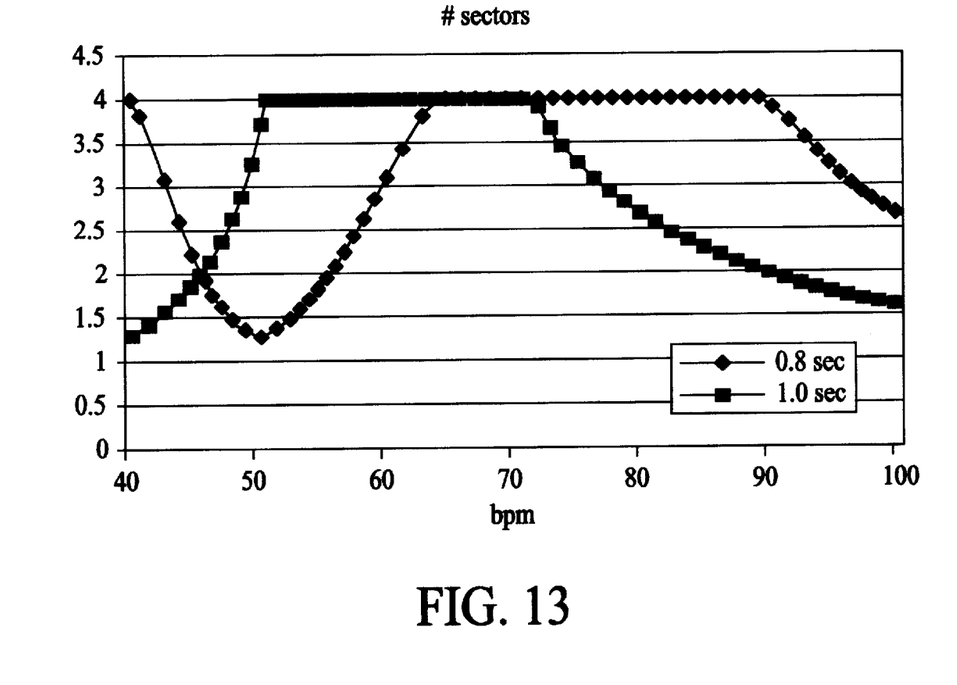
FIG. 13 is a graph the relationship between the number of sectors $n_s$ and two gantry speeds $G_s$ of 0.8 sec and 1.0 sec., where to improve stability of reconstruction and to reduce broadening of slice thickness in the table direction, $n_s$ is set to less than or equal to 4, so that there are a maximum of 4 cardiac cycles of data used for reconstruction of an image.
Figure 14:
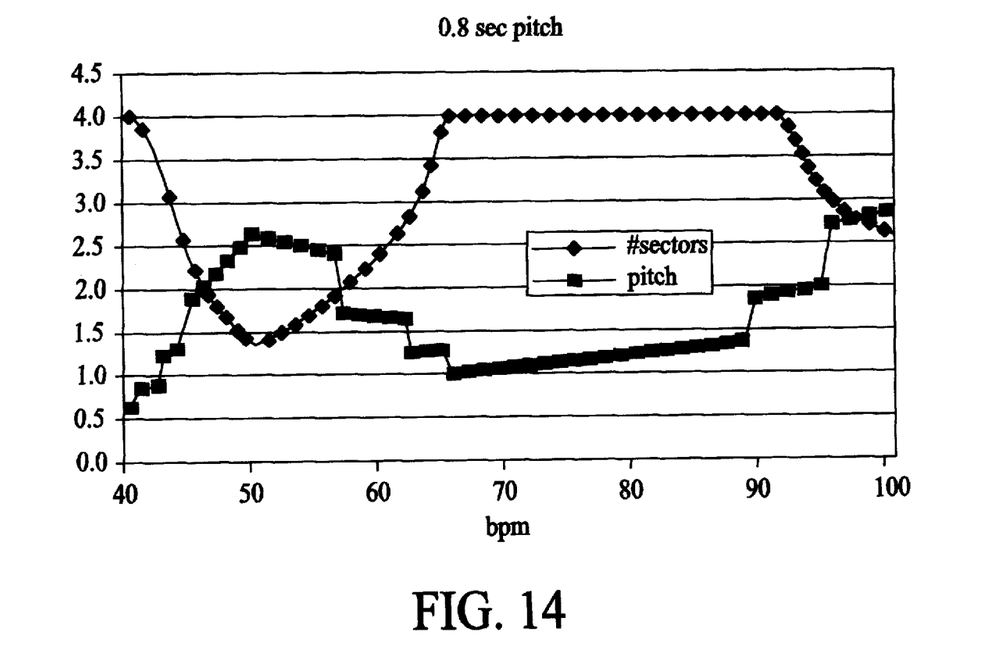
FIG. 14 is a graph showing pitch selection with respect to gantry speed of 0.8 sec.
Figure 15:
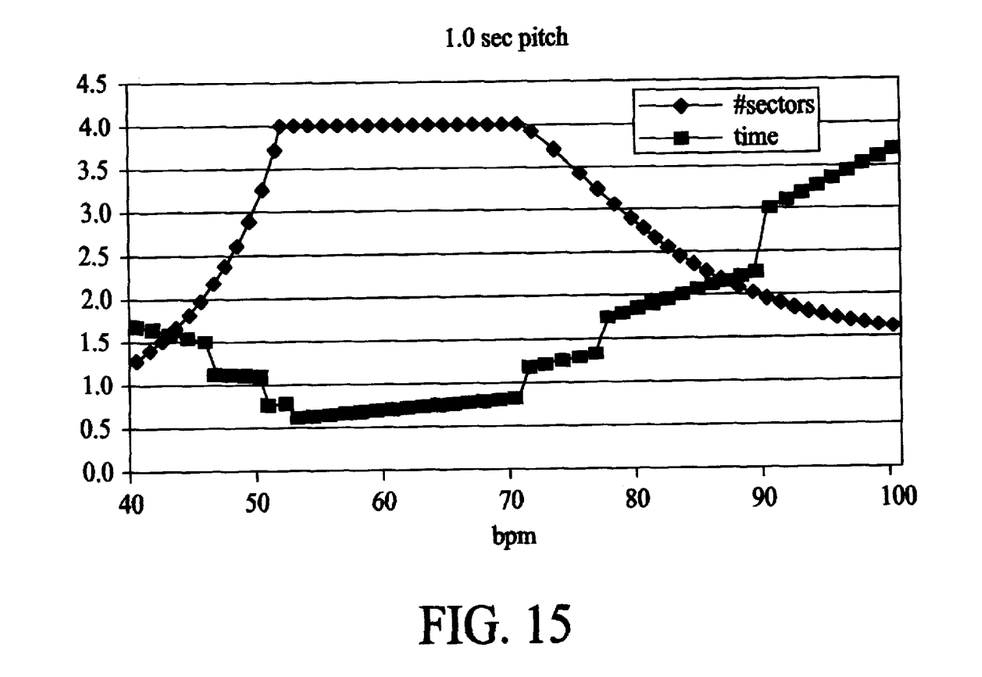
FIG. 15 is a graph showing pitch selection with respect to a gantry speed of 1.0 sec.

In one embodiment, helical pitch selection for the CT scan is based on an aligning of sectors for image reconstruction at one z-location along the table direction. Since MDCT has multiple detector rows in the table direction, data collection at one z-location is accomplished in one embodiment with two detector rows acquiring data in one cardiac cycle and a neighboring two detector rows acquiring data in the next cardiac cycle. When pitch p=1, one phase and one z-location is imaged N times with N detector rows when the gantry rotation speed matches the cardiac cycle. In one embodiment, given $n_s$, p is set as follows:

$$p = \frac{N - 1 + \lfloor n_s \rfloor}{(60/b) \times (n_s/G_s)}, \quad (11)$$

where $\lfloor n_s \rfloor$ is the fractional portion of $n_s$, i.e., $0 < \lfloor n_s \rfloor < 1$. Eq. 11 is based on the amount of distance (numerator) in detector rows that the last detector row has to travel to be in the same phase as the first detector row was to the amount of time in gantry rotations (denominator). FIG. 12 shows the relation for this computation. FIG. 13 shows the $n_s$ with respect to $G_s$=0.8 or 1.0 sec with $n_s$<4. FIGS. 14 and 15 represent pitch selection for $G_s$=0.8 and 1.0 sec, respectively.

In one embodiment, to reduce unwanted image artifacts due to the combination of the sectors from multiple cardiac cycles for image reconstruction, sector boundaries are smoothed to ensure smooth transition of one sector to the next. In another embodiment, z-interpolation is used to ensure the data of the sectors lined up at the same z-location and in yet another embodiment, enhanced z-interpolation is used to ensure more reconstruction of more slices for 3D rendering purpose.

Figure 16:
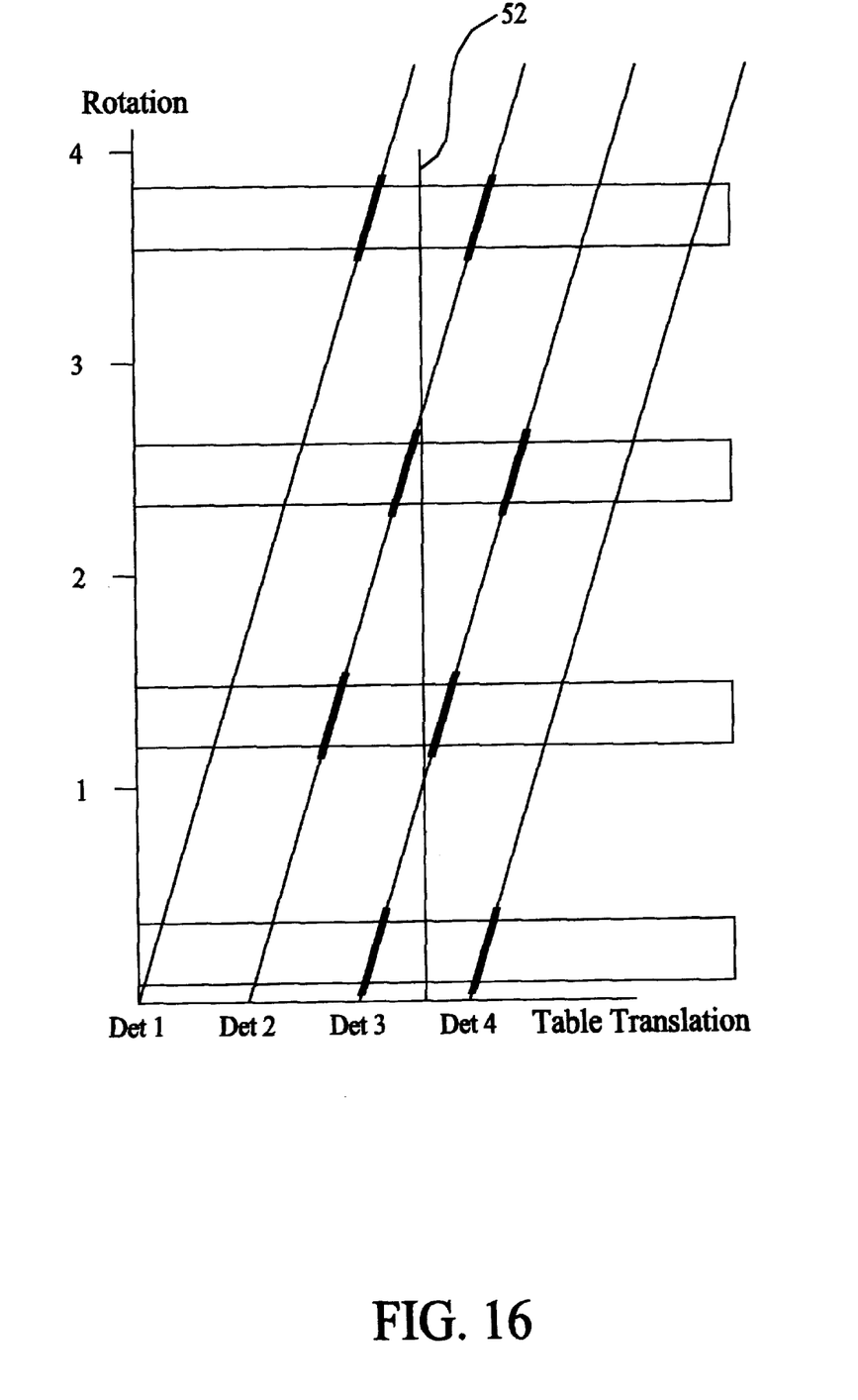
FIG. 16 is a representation of z-interpolation.

In one embodiment using Z-interpolation, linear interpolation is performed between two detector rows that are closest to the z-location of image reconstruction, as represented in FIG. 16. Once an image location is selected (shown as a solid vertical line 52 in FIG. 16), data for each view angle in the sectors (shaded) are weighted linearly.

Figure 17:
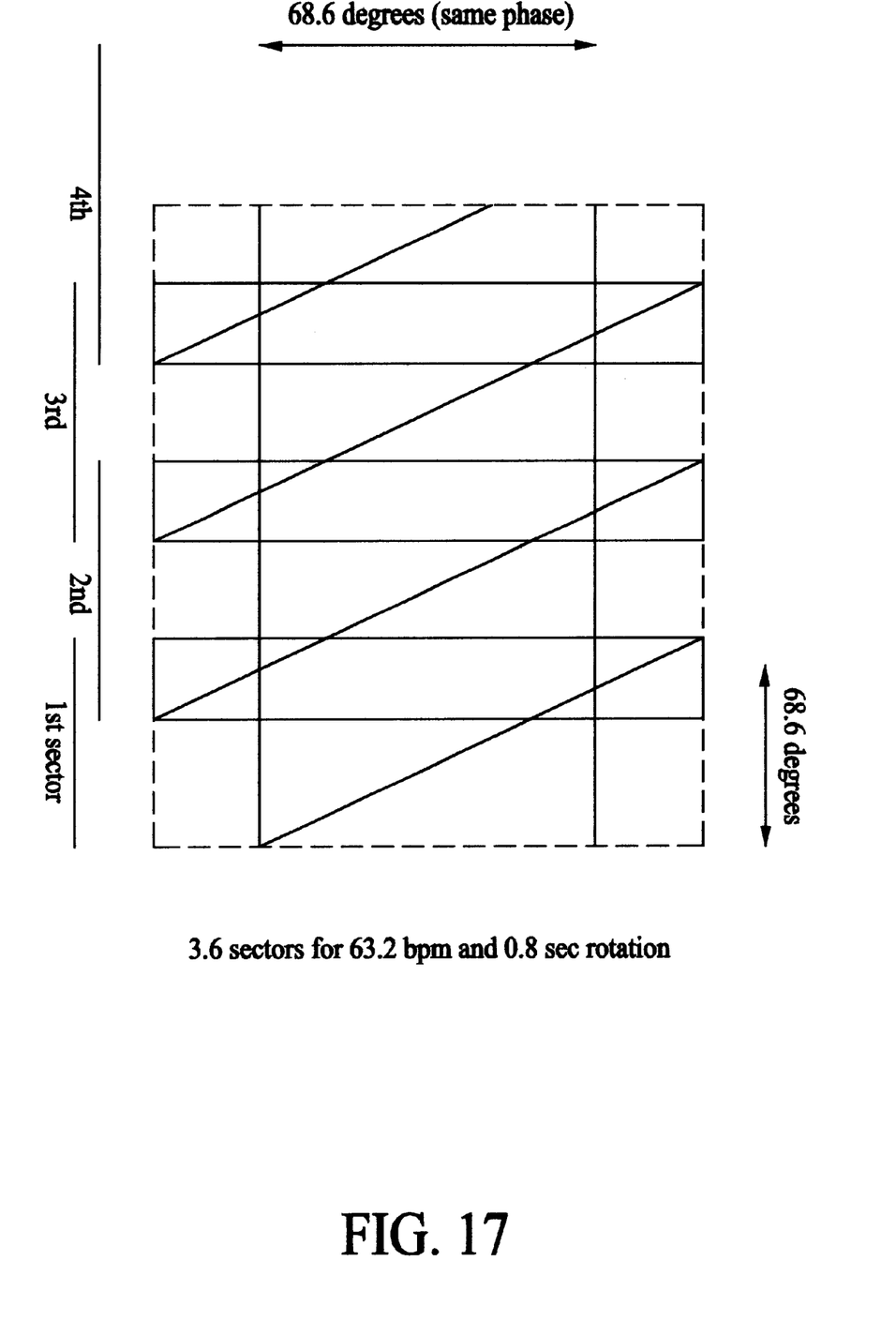
FIG. 17 is a representation of smoothing across boundaries.

Smoothing of sector boundaries is accomplished in one embodiment using an overlap of consecutive sectors and an appropriate weighting. A fraction of the sectors for reconstruction are extended, and a smoothing function is applied at a junction of the boundaries of two sectors to ensure a smooth transition from one sector to the next. This smoothing reduces streaking artifacts resulting from transition from one sector to a neighboring sector or sectors, as represented in FIG. 17.

Figure 18:
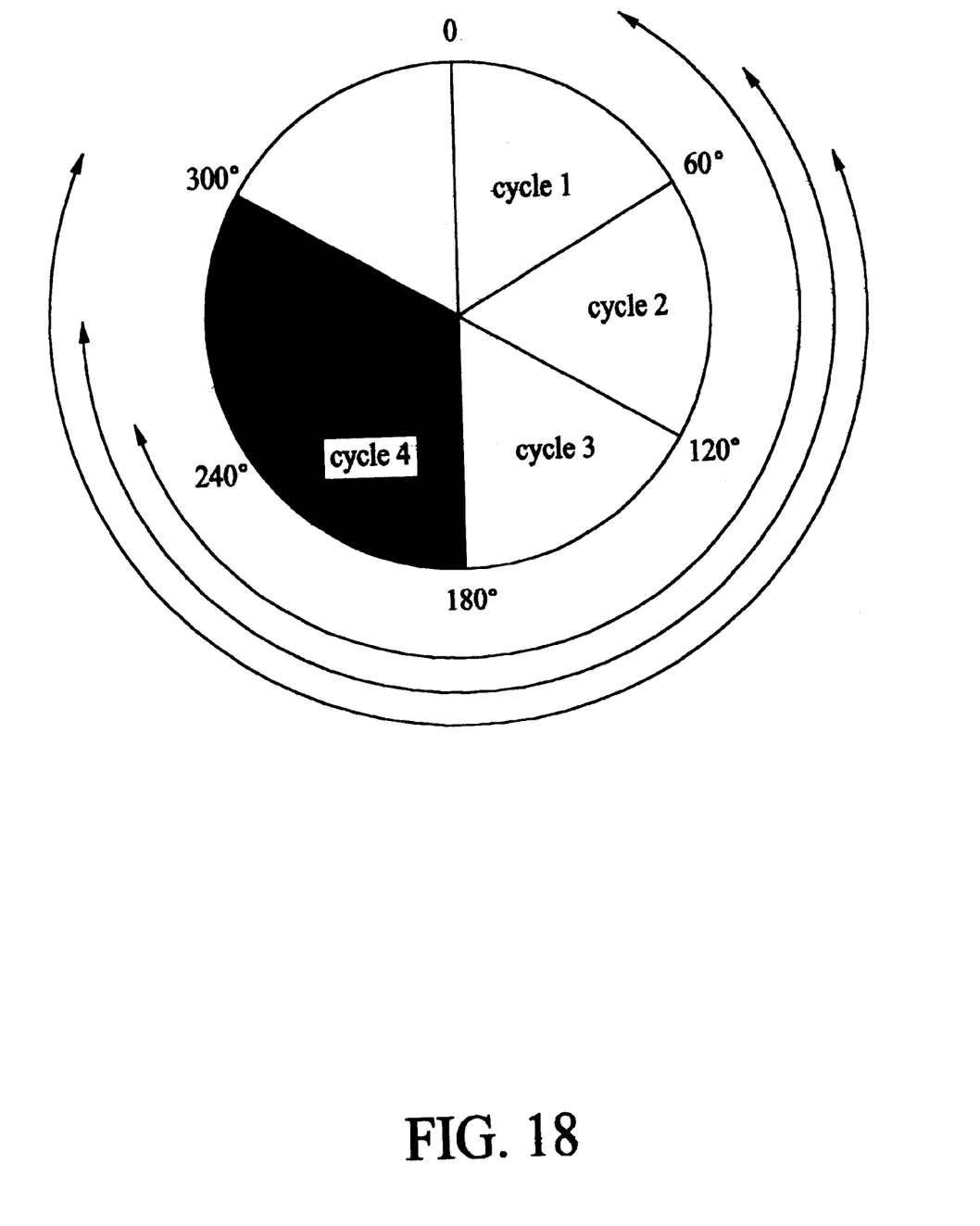
FIG. 18 is a representation of interpolation between two images.

In one embodiment, enhanced z-interpolation is used to produce many slices per cardiac cycle for 3D rendering purposes, as represented in FIG. 18. In this embodiment, the reconstruction reconstructs one image per cardiac cycle by default. Normally, this would give images with a minimum number of sectors. However, enhanced z-interpolation is used between images from a set of images corresponding to one image per cardiac cycle, because the z-location changes and the sectors used for reconstruction change according to the number of slices per cardiac cycle. FIG. 18 is a representation of the sector selection of one embodiment when 4 images per cardiac cycle are selected.

Observations of patients suggest that a heart rate variation of 10 to 15 bpm in a single breath-hold of 30 to 40 secs is not uncommon, with even greater variation near the end of scanning due to the diaphragm pushing up. Therefore, a variation of several bpms is likely to occur during 2 to 4 consecutive cardiac cycles, and this variation is well tolerated in the MSR. Some degradation of image quality may be noted at times due to patient motion, or arrhythmia. Pacer wires can also cause darkening and/or streaking in images, as well as inconsistent contrast presentation in the superior vene cava and cardiac chambers.

It will be observed that embodiments of the present invention provide higher signal to noise and/or temporal resolution from gated CT image data than is possible with conventional half-scan reconstruction. The embodiments described herein concern cardiac imaging and gating using an EKG machine 50. However, it will be understood that CT imaging of other cyclically moving objects can be improved using the apparatus and methods of this invention through use of appropriate gating signals and gantry rotation rates. For example, the present invention can be practiced with other types of cyclically moving objects by retrospectively gating the projection data of the object with a gating signal related to the motion of the cyclically moving object so that a geometric phase difference is created between a gantry rotation cycle and a cycle of the cyclically moving object.

While the invention has been described in terms of various specific embodiments, those skilled in the art will recognize that the invention can be practiced with modification within the spirit and scope of the claims.

What is claimed is:

1. A method for multisector computed tomographic (CT) imaging of a cyclically moving object comprising the steps of:
    helically scanning a cyclically moving object with a CT imaging system having multiple detector rows and a rotating gantry, at a gantry rotation speed selected either to lead or to lag a cycle of the cyclically moving object;
    retrospectively gating the projection data of the object with a gating signal related to the motion of the cyclically moving object so that a geometric phase difference is created between a cycle of the rotating gantry and the motion of the cyclically moving object; and
    reconstructing an image of the cyclically moving object using gated sector data from image data representing a plurality of consecutive cycles of the cyclically moving object.

2. A method in accordance with claim 1 wherein the cyclically moving object is a patient's heart, the cycles of the cyclically moving object are cardiac cycles, and said step of retrospectively gating the projection data of the object with a gating signal comprises the step of recording an EKG signal representative of the patient's cardiac cycle.

3. A method in accordance with claim 2 wherein said step of helically scanning a cyclically moving object with a CT imaging system comprises the step of selecting a gantry rotation speed from the group consisting of $G'_s$ and $G_s^\dagger$, where $$G'_s = \frac{360}{7B}, \text{ and } G_s^\dagger = \frac{360}{5B},$$

and B is the patient's heart rate in beats per minute.

4. A method in accordance with claim 3 wherein said step of reconstructing an image of the cyclically moving object comprises the step of reconstructing an image of the cyclically moving object using projection data representative of $n_s$=4 cardiac cycles.

5. A method in accordance with claim 3 wherein said selection of gantry rotation speed depends upon a heart rate of the patient.

6. A method in accordance with claim 2 wherein said step of helically scanning a cyclically moving object with a CT imaging system comprises the step of selecting a gantry rotation speed from the group consisting of 0.8 seconds per rotation and 1.0 seconds per rotation.

7. A method in accordance with claim 2 wherein the CT imaging system has a z-axis;
said step of helically scanning the cyclically moving object comprises the steps of moving the cyclically moving object parallel to the z-axis; and acquiring a plurality of sectors of projection data of the cyclically moving object;
said step of reconstructing an image of the cyclically moving object comprises using said plurality of sectors of projection data to reconstruct the image;
and further comprising the step of selecting a helical pitch for said helical scanning step so that sectors used for said step of reconstructing an image are aligned at the same z-axis location.

8. A method in accordance with claim 7 wherein said helical pitch p is selected as:

$$p = \frac{N - 1 + \lfloor n_s \rfloor}{(60/b) \times (n_s/G_s)},$$

where:
$\lfloor n_s \rfloor$ is the fractional portion of $n_s$;
$n_s$ is a number of cardiac cycles used for reconstruction;
B is the heart rate in beats per minute; and
$G_s$ is the gantry rotation speed in seconds per revolution.

9. A method in accordance with claim 7 wherein the sectors used for reconstruction have overlapping boundaries, and further comprising the step of applying a smoothing function at a junction of boundaries between sectors to provide a smooth transition from one sector to the next.

10. A method in accordance with claim 7 further comprising the step of weighting data by interpolation between two detector rows of the multirow detector closest to a z-location of image reconstruction.

11. A computed tomographic (CT) imaging system for imaging a cyclically moving object, said imaging system having a multirow detector and a rotating gantry, and said imaging system being configured to:
helically scan a cyclically moving object at a gantry rotation speed selected either to lead or to lag a cycle of the cyclically moving object;
retrospectively gate the projection data of the object with a gating signal related to the motion of the cyclically moving object so that a geometric phase difference is created between a cycle of the rotating gantry and the motion of the cyclically moving object; and
reconstruct an image of the cyclically moving object using gated sector data from image data representing a plurality of consecutive cycles of the cyclically moving object.

12. An imaging system in accordance with claim 11 wherein to retrospectively gate the projection data of the object with a gating signal, said system is configured to use an EKG signal representative of a patient's cardiac cycle.

13. An imaging system in accordance with claim 12 configured to helically scanning the cyclically moving object at a gantry rotation speed selected from the group consisting of $G'_s$ and $G_s^\dagger$, where $G'_s$, and $G_s^\dagger$, and B is the patient's heart rate in beats per minute.

14. An imaging system in accordance with claim 13 wherein to reconstruct an image of the cyclically moving object, said imaging system is configured to use projection data representative of $n_s = 4$ cardiac cycles.

15. An imaging system in accordance with claim 13 configured to scan at a gantry rotation speed dependent upon a heart rate of the patient.

16. An imaging system in accordance with claim 12 wherein to helically scan a cyclically moving object, said imaging system is configured to scan the cyclically moving object at gantry rotation speed selected from the group consisting of 0.8 seconds per rotation and 1.0 seconds per rotation.

17. An imaging system in accordance with claim 12 having a z-axis, said imaging system configured to:
helically scan the cyclically moving object, said imaging system is configured to move the cyclically moving object parallel to the z-axis; and acquire a plurality of sectors of projection data of the cyclically moving object;
reconstruct an image of the cyclically moving object, said imaging system is configured to use said plurality of sectors of projection data for reconstructing the image; and
scan at a helical pitch such that sectors used for reconstructing said image are aligned at the same z-axis location.

18. An imaging system in accordance with claim 17 wherein said helical pitch p is written as:

$$p = \frac{N - 1 + \lfloor n_s \rfloor}{(60/b) \times (n_s/G_s)},$$

where:
$\lfloor n_s \rfloor$ is the fractional portion of $n_s$;
$n_s$ is a number of cardiac cycles used for reconstruction;
B is the heart rate in beats per minute; and
$G_s$ is the gantry rotation speed in seconds per revolution.

19. An imaging system in accordance with claim 17 wherein the sectors used for reconstruction have overlapping boundaries, and said imaging system is further configured to apply a smoothing function at a junction of boundaries between sectors to provide a smooth transition from one sector to the next.

20. An imaging system in accordance with claim 17 further configured to weight data by interpolation between two detector rows of the multirow detector closest to a z-location of image reconstruction.

* * * * *

UNITED STATES PATENT AND TRADEMARK OFFICE
CERTIFICATE OF CORRECTION

PATENT NO. : 6,504,894 B2
DATED : January 7, 2003
INVENTOR(S) : Tin-Su Pan et al.

It is certified that error appears in the above-identified patent and that said Letters Patent is hereby corrected as shown below:

Column 2,
Line 1, place "1/2" into subscript

Column 5,
Line 3, delete "π+γ" and insert therefor -- $n+\gamma$ --.
Line 7, delete "be".
Line 47, delete "speeds" and insert therefor -- speed --.
Line 61, "$G_s^{554}$" and insert therefor -- $G_s^\dagger$ --.

Line 67, delete "n," and insert therefor -- $n_s$ --.

Column 6,
Line 14, delete "n," and insert therefor -- $n_s$ --.
Line 15, delete "$T_m$ over $T_m$" and insert therefor -- $T_m$ over $T_{1/2}$ --.
Line 43, delete "$T=T_{1/2}-T_m$" and insert therefor -- $T_r=T_{1/2}-T_m$ --.

Column 7,
Line 10, in the formula delete "(60/b)" and insert therefor -- (60/B) --.
Line 18, delete "$n_s<4$" and insert therefor -- $n_s \leq 4$ --.

Column 10,
Line 2, delete "where $G'_s$ and $G_s^\dagger$," and insert therefor -- where $$G'_s = \frac{360}{7B}, \quad \text{and} \quad G_s^\dagger = \frac{360}{5B}, \text{--}.$$

Signed and Sealed this

Twenty-second Day of July, 2003

JAMES E. ROGAN
*Director of the United States Patent and Trademark Office*